US00PP30421P3

(12) United States Plant Patent
Wheeler et al.

(10) Patent No.: US PP30,421 P3
(45) Date of Patent: Apr. 23, 2019

(54) BLUEBERRY PLANT NAMED 'BB07-7FL-4'

(50) Latin Name: *Vaccinium corymbosum*
Varietal Denomination: BB07-7FL-4

(71) Applicant: Berry Blue, LLC, Grand Junction, MI (US)

(72) Inventors: Edmund J. Wheeler, Holland, MI (US); James F. Hancock, Scarborough, ME (US)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 15/731,863

(22) Filed: Aug. 14, 2017

(65) Prior Publication Data

US 2018/0177089 P1 Jun. 21, 2018

Related U.S. Application Data

(63) Continuation of application No. 15/150,525, filed on May 10, 2016, now abandoned.

(51) Int. Cl.
*A01H 5/08* (2018.01)

(52) U.S. Cl.
USPC ..... Plt./157
CPC ..... *A01H 5/08* (2013.01)

(58) Field of Classification Search
USPC ..... Plt./157
See application file for complete search history.

*Primary Examiner* — Susan McCormick Ewoldt
(74) *Attorney, Agent, or Firm* — King IP Law; Joshua King

(57) ABSTRACT

A new and distinct cultivar of blueberry plant named 'BB07-7FL-4' as described and shown herein. 'BB07-7FL-4' is a new and distinct low chill tetraploid Southern highbush blueberry (*Vaccinium*) variety of complex ancestry, based largely on *V. corymbosum* with over 13% *V. darrowii* and small contributions of *V. angustifolium, V. tenellum*, and *V. ashei*. 'BB07-7FL-4' is a productive very early season variety. 'BB07-7FL-4' is intended for areas that successfully grow lower chill Southern highbush varieties. The fruit of 'BB07-7FL-4' are large, typically 18 mm or more in diameter with an average berry weight of 2.9 gram per berry, well exposed on a medium upright bush with a small crown. 'BB07-7FL-4' has very good flavor with a balanced amount of sugar and acidity and is also firm and juicy.

4 Drawing Sheets

Latin name: *Vaccinium corymbosum.*

BACKGROUND AND SUMMARY

Blueberries are a well-known fruit enjoyed by many throughout the world. One example of an existing, patented blueberry variety is 'Springhigh', U.S. Plant Pat. No. 16,404. Another example of an existing, patented blueberry variety is 'Snowchaser', U.S. Plant Pat. No. 19,503.

Compared to 'Springhigh', 'BB07-7FL-4' is about 5 days earlier in maturity, has a flatter shaped berry, is much lighter in color and is larger in size.

Compared to 'Snowchaser', 'BB07-7FL-4' is much larger in size, is slightly flatter shape and is much lighter in color.

The present cultivar, 'BB07-7FL-4', provides one or more advantages compared to these and/or other blueberry varieties.

BRIEF DESCRIPTION OF THE PHOTOGRAPHS

DETAILED DESCRIPTION

Figure 1:
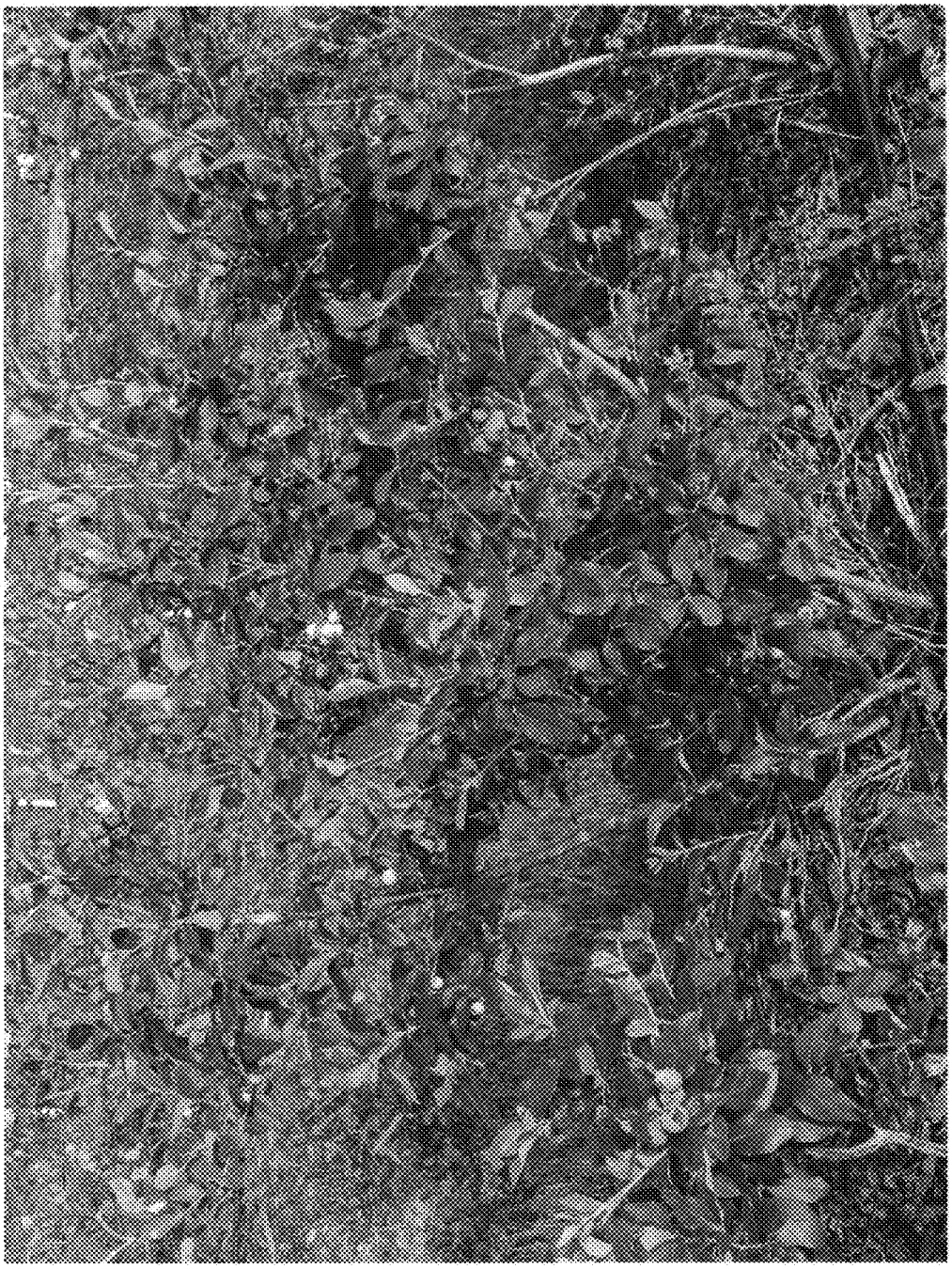
FIG. 1 is a photograph taken in April, 2015, Interlachen, Fla. of the Blueberry cultivar 'BB07-7FL-4' showing overall appearance of the variety.
Figure 2:
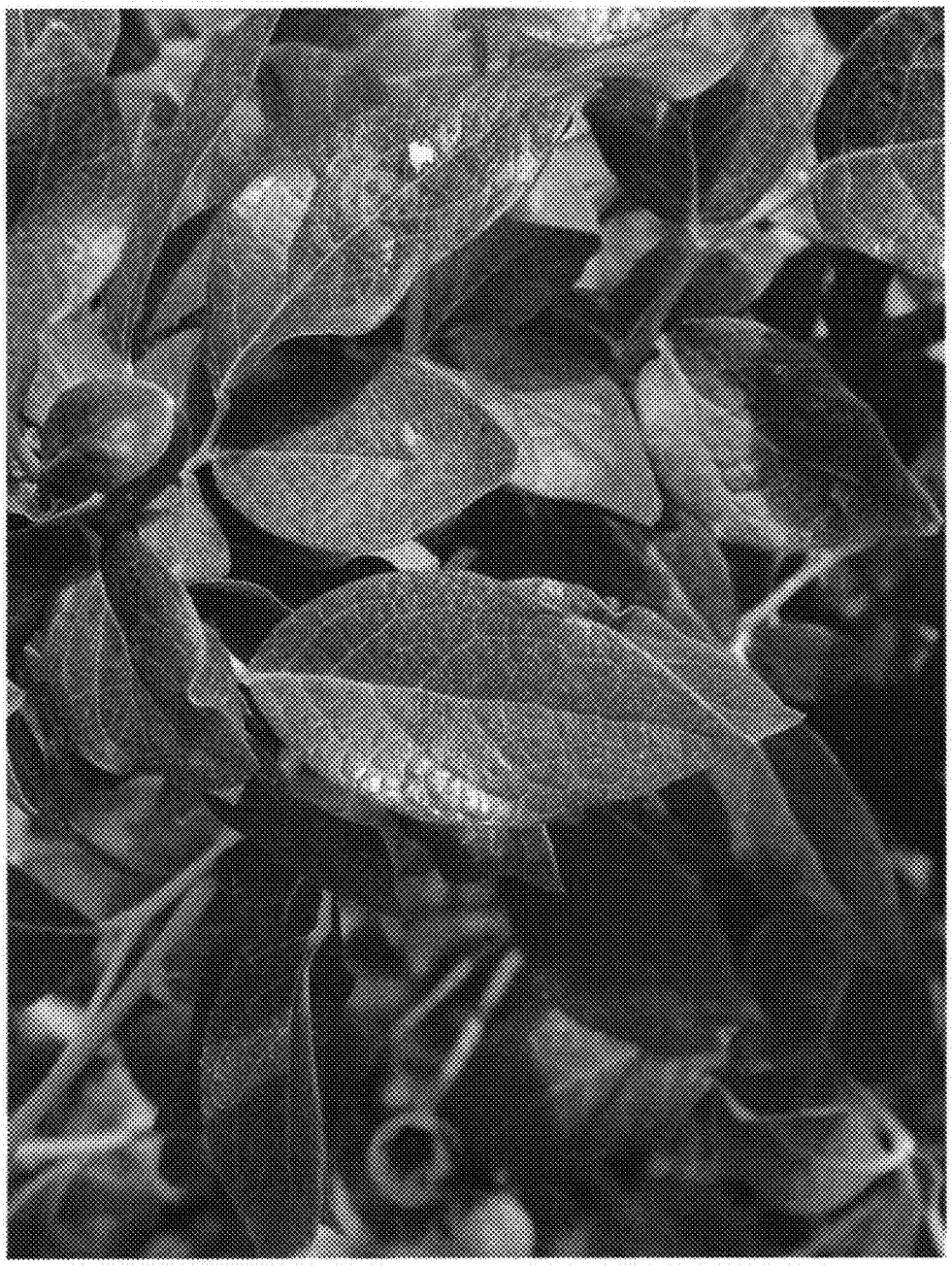
FIG. 2 is a close-up photograph taken in April, 2015, Interlachen, Fla. of the Blueberry cultivar 'BB07-7FL-4' showing the appearance of the leaves of the variety.
Figure 3:
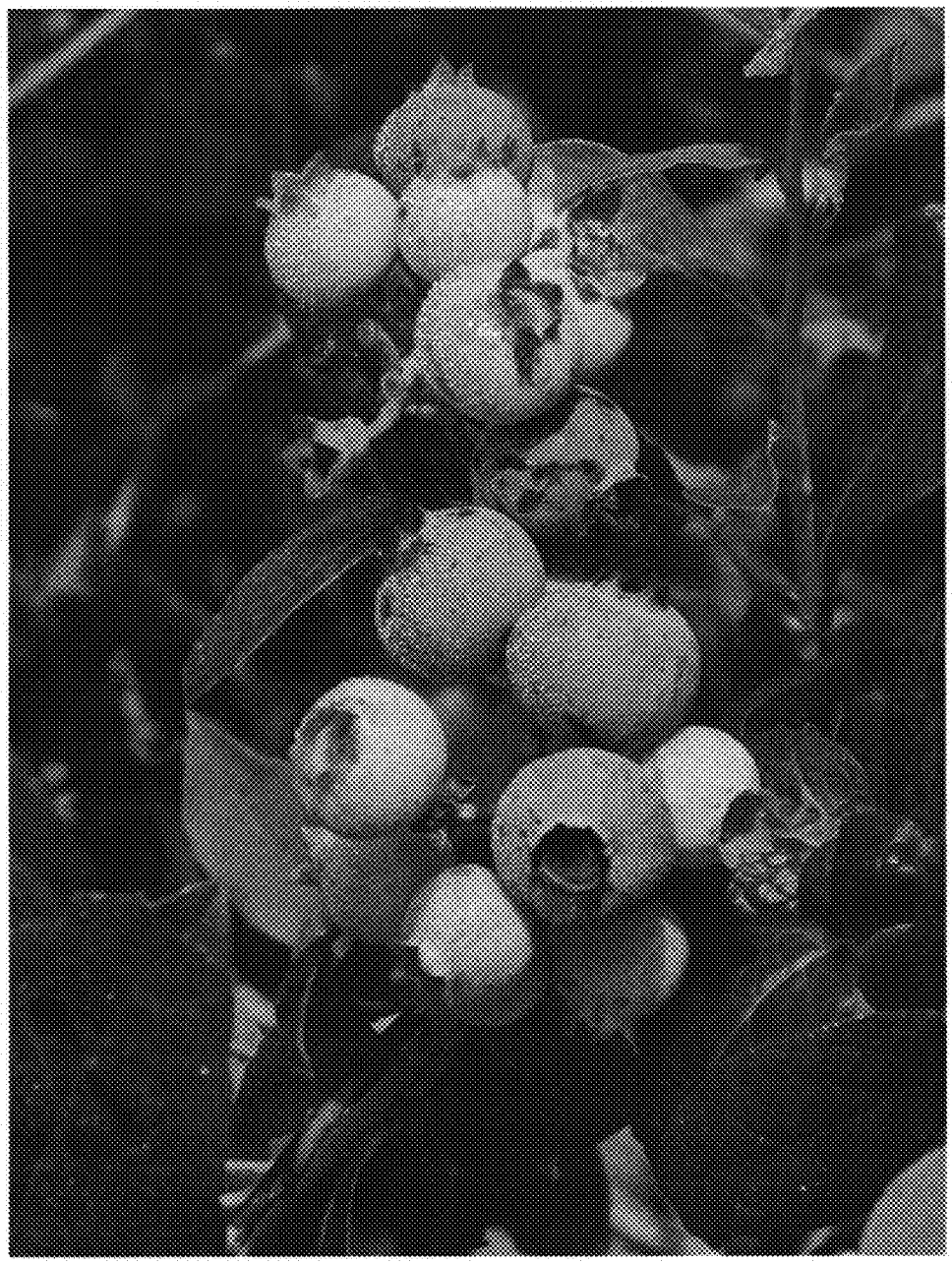
FIG. 3 is a close-up photograph taken in April, 2015, Interlachen, Fla. of the Blueberry cultivar 'BB07-7FL-4' showing a fruit cluster with ripe and unripe fruit, and also further showing the appearance of the leaves of the variety.
Figure 4:
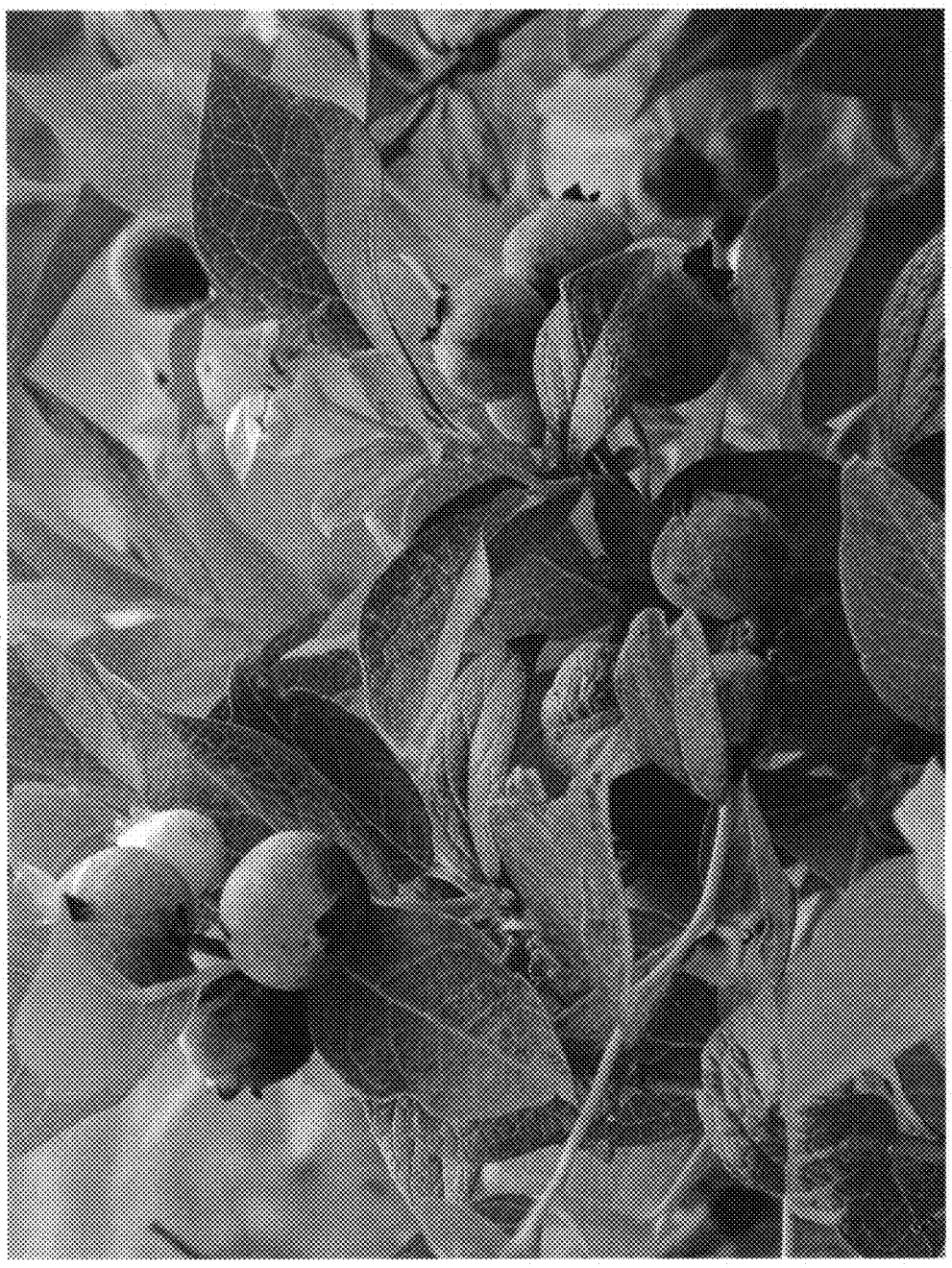
FIG. 4 is a second close-up photograph taken in April, 2015, Interlachen, Fla. of the Blueberry cultivar 'BB07-7FL-4' showing a fruit cluster with ripe and unripe fruit, and also further showing the appearance of the leaves of the variety.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from plants 5 years of age specimen plants grown in Interlachen, Fla., Manor, Ga. and Homerville, Ga. in 2011 and further observed between 2012 and 2015.

Cultivar Name: 'BB07-7FL-4'.

Classification:
Family: Ericaceae.
Botanical name: *Vaccinium corymbosum.*
Common name: Blueberry.
Parentage:
Female Parent
Name: 'Millennia'.
U.S. Plant Pat. No. 12,816.

Compared to 'Millennia', 'BB07-7FL-4' has a maturity date that is 10 days earlier. 'BB07-7FL-4' has a slightly rounder berry shape and darker blue color than 'Millennia'.

'BB07-7FL-4' also has a slightly larger size berry and much firmer berry compared to 'Millennia'.

Male Parent

'Jewel'.

U.S. Plant Pat. No. 11,807.

Compared to 'Jewel', 'BB07-7FL-4' matures 5 days earlier. 'BB07-7FL-4' has a much larger and much firmer berry than 'Jewel'. 'BB07-7FL-4' has a slightly darker blue color, and a sweeter and less acidic flavor than 'Jewel'.

'BB07-7FL-4' originated as a seedling selected from the cross 'Millennia' x 'Jewel'. The seed that gave rise to 'BB07-7FL-4' was produced by hand-pollination in a greenhouse in Grand Junction, Mich. in 2007, grown for one year in Grand Junction and then shipped to Interlachen, Fla. where it was planted in an observation nursery. In 2009, 'BB07-7FL-4' was first selected for the desirable features of early maturity, large size and excellent fruit quality and was given the designation 'BB07-7FL-4'. 'BB07-7FL-4' was first propagated by vegetative cuttings in Interlachen, Fla. for further testing in 2009. Three to five plants each were placed in advanced test plots in Interlachen, Fla., Manor, Ga. and Homerville, Ga. in 2011 and further observed between 2012 and 2015.

'BB07-7FL-4' was first asexually propagated from softwood cuttings in 2009 in Interlachen, Fla. and tissue culture since 2012 in Middleton, Wis. In all cases the propagated plants have retained the original characteristics of the original selected plant when planted in Interlachen, Fla. and Manor, Ga. The variety is able to root readily from softwood cuttings or tissue culture microshoots.

All field observations were made in 2014 and 2015 on plants located in an advanced trial planting near Interlachen, Fla., from plants propagated by vegetative cuttings from the original selected plant. Laboratory analyses of fruit characteristics were done in Grand Junction, Mich. in 2015.

General comments: 'BB07-7FL-4' is a new and distinct low chill tetraploid Southern highbush blueberry (*Vaccinium*) variety of complex ancestry, based largely on *V. corymbosum* with over 13% *V. darrowii* and small contributions of *V. angustifolium, V. tenellum*, and *V. ashei*. 'BB07-7FL-4' is a productive cultivar that ripens in the early season in northern Florida and southeast Georgia. 'BB07-07FL-4' attributes include a concentrated fruit ripening period, an upright bush shape with a small crown and has easy detachment of firm fruit for mechanical harvesting with excellent fruit quality, flavor and yield. 'BB07-7FL-4' is intended for areas that successfully grow lower chill Southern highbush varieties. The fruit of 'BB07-7FL-4' are large, typically 18 mm or more in diameter with an average berry weight of 2.9 gram per berry, well exposed on a medium upright bush with a small crown. The mean date of 50% flowering for 'BB07-7FL-4' is February 1 near Interlachen, Fla. Winter chill requirement for successful flowering and leafing is approximately 250 hours (<7° C.). Flowering and leafing are synchronous. The mean 50% ripening date for 'BB07-7FL-4' near Interlachen, Fla. is normally early April. Fruit shape is oblate with medium heavy amounts of waxy bloom that is persistent after handling. The 'BB07-7FL-4' variety has very good flavor with a balanced amount of sugar and acidity and is also firm and juicy. Storage ability in refrigeration can be 2 to 3 weeks long with little decline in quality.

References to color refer to The Pantone Book of Color, Eisemann and Herbert, Harry N. Abrams, Inc. Publishers, New York, ISBN 0-8109-3711-5, 1990.

Color measurements were taken with a SpectraMagic NX Model CR410, Konica Minolta, Japan.

Morphological characteristics reference: Plant Systematics, Jones and Luchsinger, 2 Ed., McGraw Hill, New York, ISBN 0-07-032796-3, 1986.

Firmness readings: BioWorks FirmTec2, Wamena, Kans.

Average size information:

*General description.*—Medium large bush, medium upright shape, 4 year plant 167 cm height, 147 cm width, height/width ratio 1.14:1.

*Growth.*—Excellent vigor, strong leafing, many canes.

*Productivity.*—Very good.

*Cold hardiness.*—Leaf and flower buds −5° C., open flowers and fruit −2° C.

Specific features of the variety:

Plant:

*Growth habit.*—Medium upright.

*Plant width.*—167 cm.

*Plant height.*—147 cm.

*Plant spread.*—167 cm.

*Productivity.*—6-7 lbs per mature bush.

*Cold hardiness/tolerance.*—Leaf and flower buds −5° C., open flowers and fruit −2° C.

*Chilling requirement.*—250 hours below 7° C.

*Canes.*—Moderately branched, average 8 canes per bush, average 86 cm length per cane, medium number of laterals.

*Mature cane color.*—Pantone Gray Sand 13-1010.

*Texture.*—Medium rough.

*Fruiting wood.*—Smooth, immature winter color — Pantone Baked Clay 18-1441, immature summer color — Pantone Peridot 17-0336.

*Internode length range.*—15-20 mm range, average 17 mm.

*Surface texture of new wood.*—Smooth.

*Mature canes.*—Circular in shape, 16 mm width.

*Time of beginning of leaf bud burst.*—January 15 (Interlachen, Fla.).

*Time of beginning of flowering.*—February 1 (Interlachen, Fla.).

*Time of 50% fruit ripening.*—April 2 (Interlachen, Fla. 2015).

*Disease resistance/susceptibility.*—None claimed.

Foliage:

*Leaf color.*—Upper — Pantone Thyme 19-0309, Lower — Pantone Oil Green 17-0115.

*Leaf arrangement.*—Simple Alternate.

*Leaf margins.*—Serrated.

*Leaf venation.*—Pinnate.

*Leaf apices.*—Acute.

*Leaf bases.*—Acute.

*Vein and petiole coloration.*—Pantone Willow Green 15-0525.

*Petiole length.*—3 mm.

*Petiole diameter.*—1 mm.

*Fall leaf color.*—Pantone Dark Red Brown 19-1526.

*Evergreen.*—No.

Leaf dimensions.

*Overall shape.*—Elliptic.

*Length.*—63 mm-76 mm range, average 67 mm.

*Width.*—34 mm-40 mm range, average 38 mm.

*Leaf margins.*—Serrated with many nectaries, no visible pubescence.

*Leaf surface.*—Smooth, upper and lower, no visible pubescence.

Leaf buds:
*Shape*.—Elliptic.
*Length*.—7 mm.
*Width*.—5 mm.
*Color*.—Pantone Dark Red Brown, 19-1526.

Flower:
*Flower shape*.—Urceolate.
*Flower bud number*.—Medium high.
*Flowers per cluster*.—7-8.
*Flower fragrance*.—Light floral.
*Corolla color*.—Pantone Ice 11-4803.
*Corolla length*.—12 mm.
*Corolla aperture width*.—6 mm.
*Corolla texture*.—Slightly ridged.
*Flower peduncle length*.—3 mm.
*Flower peduncle diameter*.—1 mm.
*Flower peduncle texture*.—Slightly rough.
*Flower peduncle color*.—Pantone Willow 16-0632.
*Flower pedicel length*.—8 mm.
*Flower pedicel diameter*.—1 mm.
*Flower pedicel texture*.—Smooth.
*Flower pedicel color*.—Pantone Willow 16-0632.
*Calyx* (*with sepals*).—3 mm in length.
*Calyx color*.—Pantone Sage 16-0421.
*Stamen*.—Length: 9 mm.
*Number per flower*.—10.
*Filament color*.—Pantone Buckskin 16-1342.
*Style*.—9 mm, top of ovary to stigma tip.
*Color*.—Pantone Sage 16-0421.
*Pistil*.—1 mm below corolla opening.
*Ovary color*.—Pantone Sage 16-0421.
*Anther*.—Length: 3 mm.
*Number*.—10.
*Color*.—Pantone Buckskin 16-1342.

Pollen:
*Abundance*.—Very good.
*Color*.—Pantone Winter White 11-0507.

Fruit:
*Date of* 50% *maturity*.—Apr. 2, 2015 (Interlachen, Fla.).
*Duration of ripening*.—March 24-April 17, 23 days, 2015 (Interlachen, Fla.).
*Yield*.—6-7 lbs/bush.
*Immature fruit color*.—Pantone Herbal Garden 15-0336.
*Berry color with wax*.—Pantone Sapphire Shimmer 16-4028, Spectramagic (L,a,b)-(38.74, 1.30, −1.30).
*Berry color with wax removed*.—Pantone Delft 19-4039.
*Berry flesh color*.—Pantone Frozen Dew 13-0513.
*Berry surface wax abundance*.—Moderately heavy, persistent.
*Calyx*.—4 mm width; shape is 5 pointed with slight bridging and slightly curved inward.
*Berry weight*.—2.9 grams/berry.
*Berry size*.—Height 12.75 mm, width 18.36 mm, aspect (H/W) 0.8.
*Berry shape*.—Oblate.
*Cluster density*.—Very loose.
*Average number of fruit per cluster*.—7.
*Average fruit weight per cluster*.—20 grams.
*Detachment force*.—Easy.
*Self-fruitfulness*.—Fair, will need cross pollination for maximum yield, earliness and size.
*Fruit stem scar*.—2 mm width, 0.5 mm depth, small and dry.
*Berry firmness*.—Medium firm, FirmTec: 203 g/mm.
*Berry sweetness*.—Brix° 10.8.
*Berry acidity*.—TA 0.34, pH 3.30.
*Berry flavor and texture*.—Very good, balanced sweetness and acidity, crunchy and juicy texture.
*Storage quality*.—Medium, 2-3 weeks in refrigerated storage.
*Suitability for mechanical harvesting*.—Good potential due to firm fruit, bush shape and crown size, concentration of ripening.

Seed:
*Seed abundance in fruit*.—Medium.
*Seed color*.—Pantone Copper Brown 18-1336.
*Seed dry weight*.—NA.
*Seed size*.—1.5 mm×0.75 mm.
*Possible typical market uses*.—Fresh and frozen markets, processing into jams, puree, yogurt, dehydration.

What is claimed is:

1. A new and distinct cultivar of Blueberry plant named 'BB07-7FL-4' as described and shown herein.

* * * * *